(12) United States Patent
Swamy et al.

(10) Patent No.: US 10,542,756 B2
(45) Date of Patent: *Jan. 28, 2020

(54) DISINFECTANT COMPOSITION FOR TEXTILE AND RELATED SUBSTRATES, AND METHOD OF TREATING A SUBSTRATE TO PROVIDE DISINFECTING ANTIBACTERIAL, ANTIVIRAL AND ANTIFUNGAL, WASH DURABLE, OPTIONALLY ENHANCED WITH MULTIFUNCTIONAL PROPERTIES

(71) Applicant: Green Impact Holding AG

(72) Inventors: Rohini Swamy, Mumbai (IN); Sanjeev Swamy, Mumbai (IN)

(73) Assignee: Green Impact Holding AG, Cham/Zug (CH)

( * ) Notice: Subject to any disclaimer, the term of this patent is extended or adjusted under 35 U.S.C. 154(b) by 359 days.

This patent is subject to a terminal disclaimer.

(21) Appl. No.: 15/201,341

(22) Filed: Jul. 1, 2016

(65) Prior Publication Data

US 2017/0006876 A1   Jan. 12, 2017

Related U.S. Application Data

(63) Continuation of application No. 14/370,728, filed as application No. PCT/IB2014/000309 on Mar. 12, 2014, now Pat. No. 9,487,912.

(30) Foreign Application Priority Data

Aug. 29, 2013   (IN) .......................... 2827/MUM/2013

(51) Int. Cl.
| | | |
|---|---|---|
| *A61K 33/38* | (2006.01) | |
| *A61K 33/02* | (2006.01) | |
| *A01N 59/16* | (2006.01) | |
| *A01N 43/08* | (2006.01) | |
| *A01N 47/44* | (2006.01) | |
| *D06M 16/00* | (2006.01) | |
| *A01N 43/16* | (2006.01) | |
| *A01N 43/78* | (2006.01) | |
| *A01N 55/00* | (2006.01) | |
| *D06M 15/055* | (2006.01) | |
| *B01D 39/08* | (2006.01) | |
| *C02F 1/00* | (2006.01) | |
| *D06M 11/83* | (2006.01) | |
| *D06M 13/322* | (2006.01) | |
| *D06M 13/513* | (2006.01) | |
| *D06M 15/03* | (2006.01) | |

(52) U.S. Cl.
CPC ............ *A01N 59/16* (2013.01); *A01N 43/08* (2013.01); *A01N 43/16* (2013.01); *A01N 43/78* (2013.01); *A01N 47/44* (2013.01); *A01N 55/00* (2013.01); *B01D 39/083* (2013.01); *B01D 39/086* (2013.01); *C02F 1/001* (2013.01); *D06M 11/83* (2013.01); *D06M 13/322* (2013.01); *D06M 13/513* (2013.01); *D06M 15/03* (2013.01); *D06M 15/055* (2013.01); *D06M 16/00* (2013.01); *A61L 2202/26* (2013.01); *B01D 2239/0442* (2013.01); *B01D 2239/10* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 3,072,534 A | 1/1963 | Roth et al. | |
| 4,504,541 A | 3/1985 | Yasuda et al. | |
| 5,849,311 A * | 12/1998 | Sawan .................... | A01N 25/24 424/406 |
| 6,197,072 B1 | 3/2001 | Li | |
| 6,264,936 B1 | 7/2001 | Sawan et al. | |
| 6,344,207 B1 * | 2/2002 | Goto ....................... | A01N 25/34 424/402 |
| 8,691,201 B2 | 4/2014 | Tanaka et al. | |
| 8,865,605 B2 | 10/2014 | Bender et al. | |
| 2003/0064645 A1 | 4/2003 | Worley et al. | |
| 2003/0088923 A1 * | 5/2003 | Sivik .................... | D06M 13/192 8/115.51 |
| 2003/0194415 A1 | 10/2003 | Wang et al. | |
| 2004/0137067 A1 | 7/2004 | Narang et al. | |
| 2005/0171235 A1 * | 8/2005 | Harren .................... | A61L 15/24 523/122 |
| 2006/0021150 A1 | 2/2006 | Hu et al. | |
| 2006/0117958 A1 * | 6/2006 | Sakadume ................ | A61L 9/16 96/223 |
| 2006/0222845 A1 * | 10/2006 | Deng ..................... | A01N 25/34 428/336 |

(Continued)

FOREIGN PATENT DOCUMENTS

| | | |
|---|---|---|
| CN | 1237087 A | 12/1999 |
| CN | 1920163 | 2/2007 |

(Continued)

OTHER PUBLICATIONS

Han et al. CN102505467. Jun. 2012. (Year: 2012).*

(Continued)

*Primary Examiner* — Cachet I Proctor
(74) *Attorney, Agent, or Firm* — Perkins Coie LLP

(57) ABSTRACT

A method of treating a textile substrate by applying a disinfecting treating composition comprising at least one anti-microbial agent, using an exhaust process, and subjecting the textile substrate to one or more heat treatments.

26 Claims, No Drawings

(56) References Cited

U.S. PATENT DOCUMENTS

| | | | |
|---|---|---|---|
| 2007/0048356 A1 | 3/2007 | Schorr et al. | |
| 2007/0065475 A1* | 3/2007 | Elfersy | A01N 33/12 424/405 |
| 2008/0138385 A1* | 6/2008 | Fukatsu | A01N 59/16 424/443 |
| 2008/0176085 A1* | 7/2008 | Tanaka | C03C 17/28 428/426 |
| 2009/0246258 A1* | 10/2009 | Shukla | D06M 11/42 424/443 |
| 2010/0239679 A1* | 9/2010 | Greene | A01N 25/26 424/490 |
| 2010/0291169 A1* | 11/2010 | Toreki | A61F 13/00063 424/405 |
| 2011/0023206 A1* | 2/2011 | Dunn | A41D 31/0022 2/81 |
| 2011/0081530 A1* | 4/2011 | Robinson | B29C 55/023 428/212 |
| 2011/0272619 A1* | 11/2011 | Wang | D06M 11/44 252/8.86 |
| 2013/0095240 A1 | 4/2013 | Parekh et al. | |

FOREIGN PATENT DOCUMENTS

| | | |
|---|---|---|
| CN | 100534334 C | 9/2009 |
| CN | 102864442 | 5/2014 |
| GB | 1449239 | 9/1976 |
| JP | H03241071 A | 10/1991 |
| JP | 08144199 A * | 6/1996 |
| JP | H08311766 A | 11/1996 |
| JP | H11189978 A | 7/1999 |
| JP | 2004115970 A | 4/2004 |
| JP | 2004300650 A | 10/2004 |
| JP | 2004360147 A | 12/2004 |
| JP | 2009191415 | 8/2009 |
| JP | 2009270208 A * | 11/2009 |
| WO | WO 2000/006210 | 2/2000 |
| WO | WO 2000/15897 | 3/2000 |
| WO | WO 2000/049219 | 8/2000 |
| WO | WO 2002/006579 | 1/2002 |
| WO | WO 2002/059404 | 8/2002 |
| WO | WO 2003/061721 | 7/2003 |
| WO | WO 2003/095734 | 11/2003 |
| WO | WO 2005/023023 | 3/2005 |
| WO | 2012001702 A1 | 1/2012 |
| WO | WO 2015/028852 | 3/2015 |

OTHER PUBLICATIONS

First Examination Report for Chinese Application No. 201480047474.X; dated Jun. 1, 2017; 23 pages.
Notice of Reasons for Rejection for Japanese Patent Application No. 2016-537394; dated May 23, 2017; 10 pages.
Japanese Office Action for Copending Japanese Application No. 2016-537394 with English Translation, Applicant: Green Impact Holding AG, dated Oct. 17, 2017, 5 pages.
International Search Report, International Application PCT/IB2014/000309, dated Oct. 14, 2014, 3 pages.
Written Opinion of the International Preliminary Examining Authority, International Application PCT/IB2014/000309, dated Aug. 7, 2015, 4 pages.
International Preliminary Report on Patentability, International Application PCT/IB2014/000309, dated Jan. 8, 2016, 14 pages.
JP Application No. 2018-025913 Office Action dated Mar. 25, 2019, 5 pages.
Communication pursuant to Article 94(3) EPC dated Jul. 12, 2019, European Application No. 14728269.3.

* cited by examiner

DISINFECTANT COMPOSITION FOR TEXTILE AND RELATED SUBSTRATES, AND METHOD OF TREATING A SUBSTRATE TO PROVIDE DISINFECTING ANTIBACTERIAL, ANTIVIRAL AND ANTIFUNGAL, WASH DURABLE, OPTIONALLY ENHANCED WITH MULTIFUNCTIONAL PROPERTIES

CROSS-REFERENCE TO RELATED APPLICATIONS

This application is a continuation of, and claims the benefits of and priorities to, U.S. patent application Ser. No. 14/370,728, filed on Jul. 3, 2014, which is the National Stage of International Application No. PCT/IB2014/000309 filed Mar. 12, 2014, which claims priority to India Patent Application No. 2827/MUM/2013, filed Aug. 29, 2013, all of which are incorporated herein by reference in their entirety.

FIELD OF THE INVENTION

The present invention relates to a disinfecting antimicrobial textile having essential features such as wash durability and capability for addition of multifunctional enhancements with wash durable disinfecting antimicrobial properties.

BACKGROUND OF THE INVENTION

There is a long felt need to provide effective, durable, and long lasting disinfecting characteristics to textiles used particularly for homes, hospitals, hotels, offices, industrial environments, military, police, humans, and pets etc., as they are subject to contamination by bacteria, viruses and fungi. The prevalent environment in these locations can result in the textile being not only a fertile breeding ground for these pathogens, but also a perfect substrate from which these pathogens can be spread to others resulting in infections, maybe even death, higher operational costs and waste through redundancy and rot.

Textiles are used for a variety of purposes and in a variety of environments. As such, there is a very realistic danger of microbiological contamination on the textile surfaces. Additionally, danger of staining of apparel due to ketchup, blood, sputum, honey, human excreta and moisture are also problems faced by users in various circumstances. Not only do such stains look ugly, but they also are fertile breeding grounds for various harmful bacteria, fungi and viruses on the textile surface and in its cross section.

On the inner surface of the textile, dead tissue, sweat, humidity and moisture aids the growth and spread of various pathogens. Also, garments such as jackets and overcoats, which directly don't come in contact with the skin, are also susceptible to infection transfer through contact with the inner garments, which are possibly infected. As such, it is evident that textile contamination by microbiological pathogens is a major cause for concern.

Security and military personnel, stewardesses and other airline personnel are especially prone to disease and skin problems as they may have to wear the same clothing for more than one day. Military personnel may have to wear their apparel for as much as 28 days at a stretch. Not only do these soiled apparel cause health problems to the wearer but are also the breeding grounds for the spread of bacteria, fungi and virus based diseases.

In the context of the hospitals, the presence of microbes is far more threatening. Due to the nature of the environment these textiles are used in, the needs of the textiles are much more specialized. Apart from the regular textiles worn by doctors, nurses, patients and other personnel in hospitals, doctor's clinics and other such locations, textiles used in the form of scrubs, gowns, lab coats, bed sheets and pillow cases carry microbes in various proportions. Patients sleep on sheets and pillow cases that have extremely high risk of contamination due to bacterial and microbial growth resulting from excretions of the body. The mattresses and pillows are also likely to become infected due to the fact that these aren't washed. They, in turn, can transmit infection to the patient. Sheets, pillow covers, gowns, and curtains are subjected to contamination from open wounds and other medical conditions, such as coughing, wheezing, etc. Patients' gowns are contaminated by sweat and/or human excretion such as urine, stool and vomit. This leads to the growth of microorganisms like bacteria, viruses and fungi. Healthcare workers are very often subjected to the contamination either from soiled textiles used by patients or due to excretions of the body. Medical personnel are major causes of transmitting bacterial infection from one patient to another. Current medical textiles offer no barrier protection. Provided herein below are current situations and problems thereof in hospitals:

a. Hospital or Healthcare transmitted diseases to a great extent are textile based transmissions.

b. Doctors and Patients tend to infect each other through textile contact.

c. Current methods of washing lead to damage of the textile.

d. Pillows, mattresses and curtains are rarely washed or disinfected.

e. Post wash bacteria growth is instantaneous.

f. Body residues like sweat and dead skin are breeding grounds for bacteria.

Laundry washing of regular textiles leads to excess consumption of water. Moreover, huge quantities of detergents are used to launder the clothes, and this process is excessively time consuming due to long laundry wash times. There is also a pressing need to address this problem by creating textiles which require lesser amounts of water, time and detergents to clean.

Apart from disinfection, multifunctional capabilities such as anti-staining, moisture management, sweat transportation, abrasion resistance, insect and mosquito repellent, fire retardant, antistatic, anti-pilling, UV protection and soil release are also highly desirable in textiles, as they offer many synergistic benefits to the user. These are easily adapted to the basic function of disinfection without causing any change in functionality.

Microbiologically potable water is a pressing need today. While there is availability of fresh water resources, the water therein is often found contaminated with *E. Coli* and a wide range of other disease causing microbes. Indeed, many freshwater sources are used by the local population for a variety of activities ranging from bathing, to washing of clothes, to bathing their cattle, etc. As such, the levels of contamination in most of these water resources are considerable. If used for drinking, such contaminated water could lead to outbreaks of diarrhea, cholera and a host of other diseases, as indeed evidenced by studies across the world. While systems do exist which can kill the waterborne microbiology using chemical dosing, the use of such chemicals over extended periods is harmful for the human body. Moreover, yet other systems that can separate or kill bacteria in water use electricity, which is not readily available in a large chunk of underdeveloped regions across the globe.

While many people have indigenously used textiles to sieve water and make it more potable, those textiles cannot kill microbiological pathogens. As such, there is a definite need to address the issue wherein microbiologically safe drinking water can be provided in a simple manner by combining the traditional technique of cloth filtration with a technology that can make the cloth disinfecting and able to kill disease causing microbes.

PRIOR ART OF THE INVENTION

U.S. Pat. No. 2,791,518 describes a method of importing microbial properties of articles such as textiles by immersing the article in a first aqueous solution containing a water soluble base nitrogen compound (ammonia) and a monovalent silver salt soluble in a said solution, followed by a second immersion in a second solution containing a second salt capable of ion exchange with the silver salt.

U.S. Pat. No. 527,952 discloses a method of treating fibers to render them electrically conductive as well as anti bacterial comprising immersing the fibers in a bath containing an aqueous solution of a source of divalent copper ions, reducing agent, sodium thiosulphate and a source of iodide ions, where by copper iodide adsorbed into the fibers.

U.S. Pat. No. 6,962,608, which teaches about a process for preparing an antimicrobial fiber, said process comprising a) immersing a textile in an aqueous treating solution comprising an organic acid, wherein said organic acid has a at least two carboxyl groups, b) treating said fiber with an oxidizing agent to produce a peroxycarboxylic acid function, thereby preparing an antimicrobial textile containing an average of 6 weight percent of the organic acid, which not laundered at all demonstrated over 99% reduction of *E. coli.*

Therefore, the present invention solving the problems associated with the traditional use of textiles, the inventors of the alleged invention have developed a novel and inventive composition for treating the textiles and methods of making the solution as well as methods of treating textiles using the composition. Accordingly, the objectives of the invention are enumerated below.

The primary object of the present invention is to provide any textile or substrate disinfecting, antibacterial, antiviral, antifungal and wash durable properties.

Further object of the present invention is that the disinfectant textiles provide barrier protection to the wearer.

Further, important object of the present invention is that it will prohibit complete growth of bacteria, smells, odors etc.

Very important object of the present invention is that it will drastically reduce the washing costs.

SUMMARY OF THE INVENTION

In accordance with the present invention there is provided a textile comprising a substrate which is:
  i. So treated with a combination of one, several or all of a quaternary ammonium organosilane compound, and/or silver chloride and/or other types of silver salts, and/or Poly-glucosamine, and/or propiconazole, and/or biocoated silver particles and/or poly-hexa-methylene-biguanide (herein after referred to also as "functional agents"), that the entire cross section of the substrate becomes antimicrobial, anti fungal and anti viral in nature and meets the prescribed standards to qualify as disinfecting.
  ii. So processed that the above chemistry is affixed onto the textile in a wash-durable, non-leaching manner.

The resultant fabric is mildly hydrophobic across its cross section.

The application of chemistry to the textile is done using exhaust, padding, coating or spraying processes. Drying of the textile is done using normal heat setting processes as available.

Additionally, the textile substrate can be made multifunctional by adding the required functional treatments along with the disinfecting coating, during the processing phase. In order to impart multifunctional capabilities the textiles may be treated on one or both sides of the textile, either separately or jointly, with the treating composition comprising at least one treating agent selected from the group consisting of water and oil repellents, abrasion resistant agents, antistatic agents, anti-pilling agents, easy care resins, wetting agents, wicking chemicals, softeners, mosquito repellents, UV protectors, soil releasing agents, viscosity modifiers, pH modifiers, emulsifying agents and vehicles thereof.

DESCRIPTION OF THE INVENTION

The present invention relates to providing disinfecting (antimicrobial) textiles in which the textiles (said to be a substrate) have been selected from a group consisting of woven, non woven, electro spun, drawn, bonded, crocheted or knitted textiles, and are useful for humans, animals, and the environment, in apparel, medical, home, hotels, furnishings (including upholstery), kitchen, table top, bathroom, automotive, bakeries, curtains, carpets, pet products and related applications. By textiles with disinfecting qualities we refer to the specific property wherein the textile can provide a reduction in bacterial (gram positive) contamination greater than 4 logs in less than 5 minutes as well as completely hinder the growth of Fungi.

It is an additional property obtained in the present invention to make the above-mentioned disinfecting textiles wash durable (long lasting) and functionally effective even after repeated wash cycles, mechanical rubbing, contact with liquids, or contact with vapors, with a mix of chemicals that allow for high levels of disinfecting activity, resulting in a disinfecting textile which has the capability to be additionally enhanced for multi functional capabilities.

It is an aspect of the present invention that the substrate, such as the textile substrate which needs to be treated, is typically selected from a non-limiting group of textiles consisting of natural or synthetic woven textile, drawn textile, knitted textile, crocheted textile, bonded textile or non woven textile.

The natural fabric is at least one selected from the group consisting of wool, cotton, silk, linen, hemp, ramie and jute. The formulation and the method of the present invention is also suitable for application to various textiles materials including synthetic fabric which is at least one selected from the group consisting of rayon, nylon, nonacrylic olefin acrylic polyester, PTFE, PP, PPE, carbon fiber, vinyon, saran, spandex, vinalon, aramids, modal, sulfur, polybenzimidazole fibre, PLA, lyocell, orlon, vectran and zylonacrylonitrile. The above fabric can blended from any of the above mentioned fabrics/groups, for application of the composition followed by method of application.

The disinfecting treating composition for the textile substrate comprises of a combination of one, several or all of a quaternary ammonium organosilane compound, and/or silver chloride and/or other types of silver salts, and/or Polyglucosamine, and/or propiconazole, and/or biocoated silver particles and/or poly-hexa-methylene-biguanide (herein after referred to also as "functional agents"), in a concentration range of between 0.1 to 10%, more specifically 0.1 to 4%, such that the entire cross section of the substrate becomes antimicrobial, antiviral and anti fungal in nature and meets the prescribed standards to qualify as disinfecting.

Organosilane Quaternary Amine

Molecular Structure:

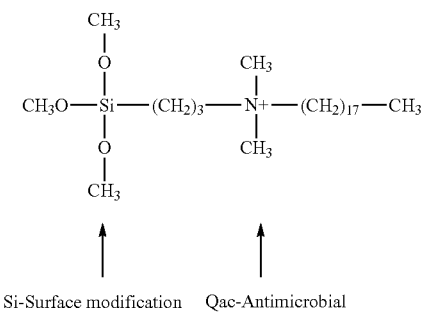

Si-Surface modification   Qac-Antimicrobial

Silver Acrylate Salt

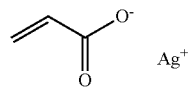

Polyhexamethylene Biguanide (PHMB)

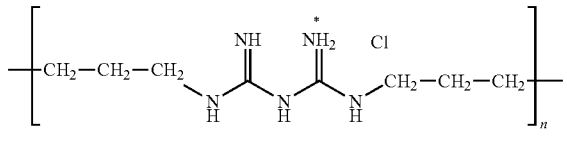

PHMB
where n is about 16

In the further embodiment of the present invention the solution and/or composition comprising of anti viral agent used to prepare disinfecting textiles is at least one selected from the group consisting of compound methyl alcohol, octadecylaminomethyl trihydroxysilylpropyl ammonium chloride and chloropropyl trihydroxysilane, poly-glucosamine, silver chloride based compound and silver chloride in aluminosilicate carrier base and polyhexamethylene biguanide, in a concentration range of between 1 ppm to 500 ppm, depending on application, and the polysaccharide or oligosaccharide or biocoated silver nanoparticles, in a concentration range of between 0.1 ppm to 150 ppm, depending on the application.

Chemical Structure of Polysaccharide

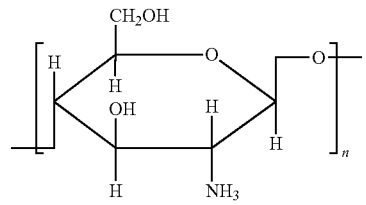

The antifungal agent is at least one selected from the group of thiabendazoles or propiconazoles in a concentration of range of between 0.5 ppm to 200 ppm, depending on application. These agents also impart a small amount of antibacterial and antiviral activity by supporting those functions through their anti fungal capabilities.

Chemical Structure of Thiabendazole

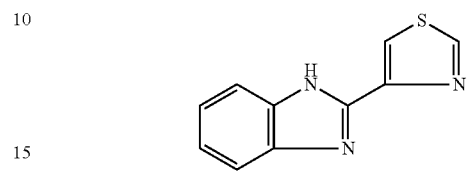

Chemical Structure of Propiconazole

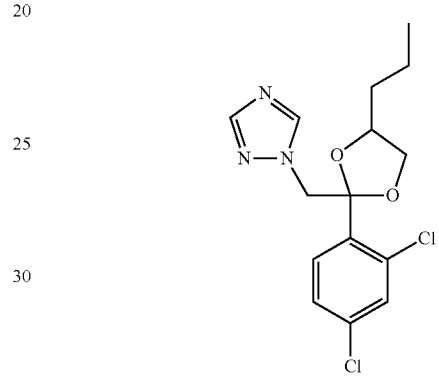

Apart from above components the present invention further includes a cross-linking agent which is selected from the type of adducts of blocked isocyanate, in a concentration range of between 1 ppm to 300 ppm, depending on application.

A further embodiment of the present invention comprises an emulsifying agent, typically, the emulsifying agent is at least one selected from the group of polyoxyethylene monostearate, polyoxyethylene, sorbitan monolaurate, polyethylene glycol 400 monolaurate in a concentration of between 0.1 ppm to 200 ppm, depending on application.

The vehicle used to prepare the solution in accordance with present composition is water or any other solvent which is compatible with the mixture of the functional agents added in the solution to create the present composition.

The treated fabric is mildly hydrophobic across its cross section. The application of chemistry to the textile is done using exhaust, padding, coating or spraying processes. Drying of the textile is done using normal heat setting processes as available.

Additionally, the textile substrate can be made multifunctional by adding the required functional treatments along with the disinfecting coating, during the processing phase. In order to impart multifunctional capabilities the textiles may be treated on one or both sides of the textile, either separately or jointly, with the treating composition comprising at least one treating agent selected from the group consisting of water and oil repellents, abrasion resistant agents, antistatic agents, anti-pilling agents, easy care resins, wetting agents, wicking chemicals, softeners, mosquito repellents, UV protectors, soil releasing agents, viscosity modifiers, pH modifiers, emulsifying agents and vehicles thereof.

In accordance with the present invention there is provided for a process for preparing a textile treated with treating composition, comprising the following method steps:

A batch of fabric is taken on the finishing machine by any one or several of four different application methods.

Padding Method i. In which method a desired concentration of finishing liquor is prepared by ad-mixing various functional agents. This finishing liquor is then fed through a pump to the padding mangle trough.

ii. Appropriate padding mangle pressure is predetermined at the time of laboratory testing prior to bulk production to obtain optimum wet pick up of the functional agents on to the textile to attain the required specifications. This is completely dependent on the quality of textile substrate, and cannot be otherwise generalized. The principle, however, is to attain enough pressure to optimize the wet pick up of the chemicals onto the textile.

iii. At this stage an admixture of organosilane, silver salts and polyhexamethylene biguanide is applied to the textile in the desired concentration ranges as mentioned above, which when polymerized are mildly hydrophobic in nature.

Exhaust Method i. A desired concentration of finishing liquor is prepared by ad-mixing various functional agents and textile substrate is treated by exhaust method means, treated in finishing liquor for specific time, temp and pH which is predetermined at the time of laboratory testing prior to bulk production to obtain optimum exhaustion of the functional agents onto the fabric to attain the required specifications.

ii. At this stage an admixture of organosilane, silver salts and polyhexamethylene biguanide is applied to the textile in the desired concentration ranges as mentioned above, which when polymerized are mildly hydrophobic in nature.

Coating Method i. A desired concentration of finishing liquor is prepared by ad-mixing various functional agents. This finishing liquor is then fed through a pump to the knife coating machine.

ii. The clearance between the textile and the knife is determined based on the required thickness of coating and the nature of the textile substrate in terms of its pick-up ability.

iii. An admixture of organosilane, silver salts and polyhexamethylene biguanide is then additionally applied to the textile, using the knife coating technique, in the desired concentration ranges as mentioned above, which when polymerized are mildly hydrophobic in nature.

Spraying Method i. A desired concentration of finishing liquor is prepared by ad-mixing various functional agents and textile substrate is sprayed with this liquor for a specific time and in temperature range of 20-90 degrees Centigrade depending on the nature of the textile substrate. The time for spraying is predetermined at the time of laboratory testing prior to bulk production to obtain optimum liquor pick-up onto the fabric to attain the required specifications of disinfection.

ii. An admixture of organosilane, silver salts and polyhexamethylene biguanide is subsequently sprayed on the textile in the desired concentration ranges as mentioned above, at a temperature range of between 20-90 degrees (depending on the nature of the textile substrate) which when polymerized are mildly hydrophobic in nature. The time of spraying is set to between 3 and 15 seconds.

2. Any one of the application processed fabric then passes through the stenter frame which provides heat of between 110° C.-180° C. with a dwell time of between 1-7 minutes, depending on the exact textile substrate and the nature of finished product application required, and the applied chemistry is partially polymerized onto the textile. The fabric is in a dry state. By this process the mildly hydrophobic fabric is then once again wound in a roll on the "A frame".

3. A mixture of cross linking agents can optionally be poured in the finishing bath of the padding mangle. Appropriate padding mangle pressure is predetermined at the time of laboratory testing prior to bulk production to obtain optimum wet pick up of the functional agents onto the fabric to attain the required specifications.

4. The fabric is then once again passed through the stenter frame for drying at a temperature of 110° C.-180° C. with a dwell time of 1-7 minutes depending on the nature of the textile substrate used and the specific application requiring the textile. At this stage, the initial antimicrobial agents applied in the first step are fully polymerized due to the heat and therefore block the textile yarns from absorbing any further chemical agents into them. The moisture cross linker however is also attached and therefore the capability of additional chemicals being attached to the surface of the textile of the yarn, without penetrating the yarn in any significant way is achieved.

5. At this stage, the textile is disinfecting in nature and has the capability of attaching, to the surface of the textile or yarn, additional technologies depending on the application. The cross section of the textile is mildly hydrophobic but, due to the presence of the moisture cross linker, adhesion of additional chemicals on the surface of the textile is made possible.

The fixation of the chemicals by complete polymerization is a non-leaching and wash durable process. As such, the resultant textile can withstand several washes without losing efficacy.

The pre-treatment of the textile substrate includes:

1. Testing the textile at laboratory scale to verify and confirm that it meets the above selection criteria, prior to production, 2. Batching and stitching together of individual textile pieces on an "A" frame.

Thorough inspection of the textile for defects during batching,

The invention will now be explained with the help of following non-limiting examples.

Example 1

Disinfecting Textile for Application in Water Filtration 0.5 to 2% add-on of octadecylaminomethyl trihydroxysilylpropyl ammonium chloride, 1 to 2% add-on of silver chloride based compound and 1 to 2% polyhexamethylene biguanide, 1 to 3% of polyglucosamine are applied onto the textile substrate through aqueous media by exhaust process at mildly acidic condition followed by heat treatment polymerization at between 130° C. and 160° C., which imparts disinfecting property to textile substrate across the entire cross section along with mildly hydrophobic performance.

Example 2

Disinfecting Textile for Application in Kitchen Towels 10 to 20 g/l of octadecylaminomethyl trihydroxysilylpropyl ammonium chloride, 10 to 20 g/l of silver chloride based compound, silver chloride in aluminosilicate carrier base, 10 to 20 g/l of polyhexamethylene biguanide are applied onto the textile substrate through aqueous media by pad impregnation method with 60 to 80% wet pickup at mildly acidic condition followed by heat treatment polymerization at between 130° C. and 160° C., which imparts antimicrobial property to textile substrate across the cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at 120° C. to 150° C., which gets bonded to the textile substrate from both sides and creates the reactant moiety to other functionality finishes that can make it superabsorbent.

Example 3

Disinfecting Textile for Application in Undergarments and Socks 0.1 to 2% add-on of octadecylaminomethyl trihydroxysilylpropyl ammonium chloride, 0.1 to 2% add-on of silver chloride based compound, silver chloride in aluminosilicate carrier base, 0.1% to 2% add-on polyhexamethylene biguanide are applied onto the textile substrate through aqueous media by coating process at mildly acidic condition followed by heat treatment polymerization at between 130° C. and 170° C., which imparts antimicrobial property to textile substrate across the entire cross section which displays disinfectant like qualities along with mildly hydrophobic performance, 5 to 20 gm/lit of blocked isocyanate based thermoplastic polymer dispersion and 1 to 18 gm/lit thiabendazole, 5 to 20 gm/lit of poly-glucosamine oligosaccharide are applied onto the above antimicrobially treated textile substrate at 120° C. to 160° C., which gets bonded to the textile substrate from both sides and creates the reactant moiety to other functionality finishes that can increase the absorbency of the garments.

Example 4

Disinfecting Textile for Application in Medical Garments where one sided sweat absorbency coating is required to be further applied 20 to 50 g/l of octadecylaminomethyl trihydroxysilylpropyl ammonium chloride, 20 to 50 g/l of silver chloride based compound, silver chloride in aluminosilicate carrier base, and 20 to 50 g/l of polyhexamethylene biguanide are applied onto the textile substrate through aqueous media by pad impregnation method with 60% to 80% wet pickup at mildly acidic condition followed by heat treatment polymerization at between 110° C. and 150° C., which imparts antimicrobial property to textile substrate across the cross section which displays disinfectant like qualities along with mildly hydrophobic performance. 5 to 15 gm/lit of blocked isocyanate based thermoplastic polymer dispersion and 1 to 20 gm/lit thiabendazole, 1 to 15 gm/lit of poly-glucosamine oligosaccharide are applied onto the above antimicrobially treated textile substrate at between 110° C. and 150° C., which gets bonded to the textile, in order to make it reactive to further coating for sweat absorbency.

Example 5

Disinfecting Textile for Application in Medical Garments Where Both Sides Need to be Made Additionally Repellant to Water, Blood and Other Fluids 0.5 to 2% add-on of octadecylaminomethyl trihydroxysilylpropyl ammonium chloride, 1 to 2% add-on of silver chloride based compound, silver chloride in aluminosilicate carrier base, and 1 to 2% polyhexamethylene biguanide are applied onto the textile substrate through aqueous media by exhaust process at mildly acidic condition followed by heat treatment polymerization at between 120° C. and 140° C., which imparts antimicrobial property to textile substrate across the entire cross section which displays disinfectant like qualities along with mildly hydrophobic performance.

5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety to further apply the fluid repellant coating.

Example 6

Disinfecting Textile for Application in Military Battle Garments Where the Textile Must be Compatible to Add Insect Repellant Treatment 10 to 50 g/l of octadecylaminomethyl trihydroxysilylpropyl ammonium chloride, 10 to 50 g/l of silver chloride based compound, silver chloride in aluminosilicate carrier base, 10 to 50 g/l of polyhexamethylene biguanide are applied onto the textile substrate through aqueous media by pad impregnation method with 60 to 80% wet pickup at mildly acidic condition followed by heat treatment polymerization at between 120° C. and 140° C., which imparts antimicrobial property to textile substrate across the cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety to apply insect repellant treatment.

Example 7

Disinfecting Textile for Application in Military Battle Garments Where the Textile Must be Compatible to Add UV Reflecting and Water Repellant Treatment 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by exhaust process at mildly acidic condition followed by heat treatment polymerization at between 130° C. and 135° C., which imparts antimicrobial property to textile substrate across the entire cross section which displays disinfectant like qualities along with mildly hydrophobic performance. b) Cross linker 2 to 18 gm/lit of blocked isocyanate based thermoplastic polymer dispersion and 1 to 18 gm/lit thiabendazole, 5 to 20 gm/lit of poly-glucosamine oligosaccharide are applied onto the above antimicrobially treated textile substrate at between 120° C. and 140° C., which gets bonded to the textile substrate from both sides and creates the reactant moiety to add UV reflecting and water repellant treatment.

Example 8

Disinfecting Textile for Application in Sweat Absorbent T-Shirts 2 to 5 add-on of octadecylaminomethyl trihydroxysilylpropyl ammonium chloride, 2 to 5% add-on of silver chloride based compound, silver chloride in aluminosilicate carrier base, are applied onto the textile substrate through aqueous media by exhaust process at mildly acidic condition followed by heat treatment polymerization at between 120° C. and 130° C., which imparts antimicrobial property to textile substrate across the cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety for other functionality finishes.

Example 9

Disinfecting Textile for Application in T-Shirts with Capability for Water Repellant, Mosquito Repellant and UV Reflecting Treatments 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by exhaust process at mildly acidic condition followed by heat treatment polymerization at between 120° C. and 130° C., which imparts antimicrobial property to textile substrate across the entire cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety to other functionality finishes.

Example 10

Disinfecting Textile for Application in Bedsheets for Hotel Industry with Capability for Addition of Mosquito Repellent Treatment 1 to 5% add-on of octadecylaminomethyl trihydroxysilylpropyl ammonium chloride, 1 to 2% add-on of silver chloride based compound, silver chloride in aluminosilicate carrier base, 1 to 5% add-on of polyhexamethylene biguanide are applied onto the textile substrate through aqueous media by spraying process at mildly acidic condition followed by heat treatment polymerization at between 130° C. and 160° C., which imparts antimicrobial property to textile substrate across the entire cross section which displays disinfectant like qualities along with mildly hydrophobic performance, 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety to other functionality finishes.

Example 11

Disinfecting Textile for Application in Bedsheets for Hotel Industry with Capability for Addition of Flame Retardant Treatment 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by exhaust process at mildly acidic condition followed by heat treatment polymerization at between 130° C. and 160° C., which imparts antimicrobial property to textile substrate across the entire cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the functionality necessary for addition of the flame retardant treatment.

Example 12

Disinfecting Textile for Application as Curtains with Capability for Addition of Flame Retardant Treatment and Water Repellency 10 to 50 g/l of octadecylaminomethyl trihydroxysilylpropyl ammonium chloride, 10 to 50 g/l of silver chloride based compound, silver chloride in aluminosilicate carrier base, 10 to 50 g/l of polyhexamethylene biguanide are applied onto the textile substrate through aqueous media by pad impregnation method with 60 to 80% wet pickup at mildly acidic condition followed by heat treatment polymerization at between 130° C. and 160° C., which imparts antimicrobial property to textile substrate across the cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety to apply the desired finish.

Example 13

Disinfecting Textile for Application in Children's Clothing 10 to 50 g/l of octadecylaminomethyl trihydroxysilylpropyl ammonium chloride, 10 to 50 g/l of silver chloride based compound, silver chloride in aluminosilicate carrier base, 10 to 50 g/l of polyhexamethylene biguanide are applied onto the textile substrate through aqueous media by spraying method with 60 to 80% wet pickup at mildly acidic condition followed by heat treatment polymerization at between 120° C. and 150° C., which imparts antimicrobial property to textile substrate across the cross section which displays disinfectant like qualities along with mildly hydrophobic performance.

Example 14

Disinfecting Textile for Application in School Uniforms 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by exhaust process at mildly acidic condition followed by heat treatment polymerization at between 130° C. and 150° C., which imparts antimicrobial property to textile substrate across the entire cross section which displays disinfectant like qualities along with mildly hydrophobic performance, 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 110° C. to 160° C., which gets bonded to the textile substrate from both sides and creates the reactant moiety to other functionality finishes.

Example 15

Disinfecting Textile for Application in Hotel Bathing Towels 20 to 50 g/l of octadecylaminomethyl trihydroxysilylpropyl ammonium chloride, 20 to 50 g/l of silver chloride based compound, silver chloride In aluminosilicate carrier base, and 20 to 50 g/l polyhexamethylene biguanide are applied onto the textile substrate through aqueous media by pad impregnation method with 60% to 80% wet pickup at mildly acidic condition followed by heat treatment polymerization at between 120° C. and 140° C., which imparts antimicrobial property to textile substrate across the cross section which displays disinfectant like qualities along with mildly hydrophobic performance.

Example 16

Disinfecting Textile for Application in Upholstery 0.5 to 2% add-on of octadecylaminomethyl trihydroxysilylpropyl ammonium chloride, 1 to 2% add-on of silver chloride based compound, silver chloride in aluminosilicate carrier base, and 1 to 2% polyhexamethylene biguanide are applied onto the textile substrate through aqueous media by exhaust process at mildly acidic condition followed by heat treatment polymerization at between 110° C. and 150° C., which imparts antimicrobial property to textile substrate across the entire cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at between 120° C. and 150° C., which gets bonded to the textile substrate from both sides and creates the reactant moiety for adding any other required treatment finishes.

Example 17

Disinfecting Textile for Application in Dog Beds with Additional Capacity for Abrasion Resistance Treatment 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by exhaust process at mildly acidic condition followed by heat treatment polymerization at between 130° C. and 135° C., which imparts antimicrobial property to textile substrate across the entire cross section which displays disinfectant like qualities along with mildly hydrophobic performance. 5 to 20 gm/lit of blocked isocyanate based thermoplastic polymer dispersion and 1 to 20 gm/lit thiabendazole, 5 to 20 gm/lit of poly-glucosamine oligosaccharide are applied onto the above antimicrobially treated textile substrate at 120° C. to 150° C., which gets bonded to the textile substrate from both sides and creates the reactant moiety to add abrasion resistant treatment.

Example 18

Disinfecting Textile for Application in Diapers for Incontinence 10 to 40 g/l of octadecylaminomethyl trihydroxysilylpropyl ammonium chloride, 10 to 40 g/l of silver chloride based compound, silver chloride in aluminosilicate carrier base, and 10 to 40 g/l of polyhexamethylene biguanide are applied onto the textile substrate through aqueous media by spraying method at mildly acidic condition followed by heat treatment polymerization at between 130° C. and 145° C., which imparts antimicrobial property to textile substrate across the cross section which displays disinfectant like qualities along with mildly hydrophobic performance. 10 to 20 gm/lit of blocked isocyanate based thermoplastic polymer dispersion and 1 to 20 gm/lit thiabendazole, 5 to 15 gm/lit of poly-glucosamine oligosaccharide are applied onto the above antimicrobially treated textile substrate at between 110° C. to 140° C., which gets bonded to the textile substrate from both sides and creates the reactant moiety to add the absorbent treatments required.

Example 19

Disinfecting Textile for Application in Air Filtration Systems 20 to 50 g/l of octadecylaminomethyl trihydroxysilylpropyl ammonium chloride, 20 to 50 g/l of silver chloride based compound, silver chloride in aluminosilicate carrier base, are applied onto the textile substrate through aqueous media by pad impregnation method with 60% to 80% wet pickup at mildly acidic condition followed by heat treatment polymerization at between 130° C. and 145° C. which imparts antimicrobial property to textile substrate across the cross section which displays disinfectant like qualities along with mildly hydrophobic performance.

Example 20

Disinfecting Textile for Application in Bandages 0.5 to 2% add-on of octadecylaminomethyl trihydroxysilylpropyl ammonium chloride, 1 to 2% add-on of silver chloride based compound, silver chloride in aluminosilicate carrier base, 1 to 2% add-on of polyhexamethylene biguanide are applied onto the textile substrate through aqueous media by coating process at mildly acidic condition followed by heat treatment polymerization at between 110° C. to 140° C., which imparts antimicrobial property to textile substrate across the entire cross section which displays disinfectant like qualities along with mildly hydrophobic performance.

We claim:
1. A method of treating a textile substrate by:
applying a disinfecting treating composition comprising at least one anti-microbial agent selected from the group consisting of a quaternary ammonium organosilane compound, a silver salt, poly-glucosamine, propiconazole, thiabendazole, biocoated silver particles, and polyhexamethylene biguanide;
using an exhaust process;
subjecting the textile substrate to a heat treatment at a temperature of between 110° C.–180° C.; and
once again subjecting the textile substrate to a heat treatment at a temperature of 110° C.–180° C.; and
wherein the disinfecting treating composition further comprises a cross-linking agent which is selected from a type of adducts of blocked isocyanate.
2. The method of 1, wherein the textile substrate, is selected from the group consisting of natural or synthetic woven, knitted, crocheted, bonded or non-woven textile.
3. The method of claim 1, wherein the textile substrate is a yarn which is spun, electrospun, drawn or extruded, or a natural fabric which is at least one selected from the group consisting of wool, cotton, silk linen, hemp, ramie and jute, or a synthetic fabric which is at least one selected from the group of rayon, nylon, non-acrylic olefin, acrylic polyester, PTFE, PP, PPE, carbon fiber, polybenzimidazole fibre, PLA.
4. The method of claim 3, wherein the fabric or yarn is blended.
5. The method of claim 1, wherein the disinfecting treating composition is used in a concentration range of between 0.1 to 10%.
6. The method of claim 1, wherein the disinfecting treating composition comprises a combination of two or more of a quaternary ammonium organosilane compound, a silver salt, polyglucosamine, propiconazole, thiabendazole biocoated silver particles and polyhexamethylene biguanide.
7. The method of claim 1, wherein the disinfecting treating composition comprises at least a combination of one selected from the group consisting of a silver salt, biocoated silver particles, and any mixture(s) thereof and a quaternary ammonium organosilane compound.
8. The method of claim 7, wherein the combination further comprises polyhexamethylene biguanide, or polyhexamethylene biguanide and polyglucosamine.
9. The method of claim 1, wherein the disinfecting treating composition comprises thiabendazole and polyglucosamine.

10. The method of claim 1, wherein a quaternary ammonium organosilane compound having the molecular structure,
Organosilane quaternary amine
Molecular Structure:

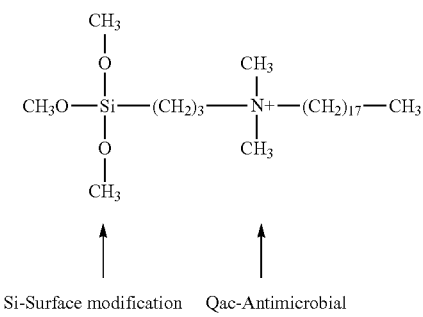

is used in the range of 0.5%-5%.
11. The method of claim 10, wherein the quaternary ammonium organosilane is an octadecylaminomethyl trihydroxysilylpropyl ammonium chloride, used in the range of 5 to 50 gram by weight.
12. The method of claim 1, wherein a silver acrylate salt of the disinfecting treating composition is used in the range of 0.1% to 5%,
Silver acrylate salt

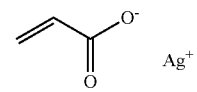

and the polyhexamethylene biguanide (PHMB) used in the range of 1 to 2%, or 2 to 50 grams by weight,
Polyhexamethylene Biguanide (PHMB)

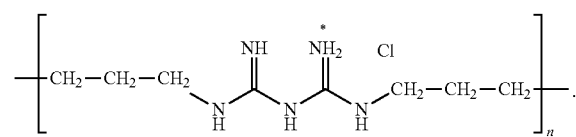

PHMB
where n is about 16

13. The method of claim 1, wherein the disinfecting treating composition further comprises an anti-viral agent selected from the group consisting of compound methyl alcohol, octadecylaminomethyl trihydroxysilylpropyl ammonium chloride and chloropropyl trihydroxysilane, poly-glucosamine, silver chloride based compound and silver chloride in an aluminosilicate carrier base and polyhexamethylene biguanide.
14. The method of claim 1, wherein the disinfecting treating composition further comprises an anti-fungal agent comprising one selected from the group of thiabendazoles and propiconazoles.
15. The method of claim 1, wherein the disinfecting treating composition further comprises an emulsifying agent which is at least one selected from the group of polyoxyethylene monostearate, polyoxyethylene sorbitan monolaurate, polyethylene glycol 400 monolaurate.

16. The method of claim 1, wherein water, or any other solvent which is compatible with the at least one anti-microbial agent is added as a vehicle.

17. The method of claim 1, wherein the disinfecting treating composition further comprises at least one treating agent selected from the group consisting of water and oil repellents, abrasion resistant agents, antistatic agents, anti-pilling agents, easy care resins, wetting agents, wicking chemicals, softeners, mosquito repellants, UV protectors, soil releasing agents, viscosity modifiers, pH modifiers, emulsifying agents and vehicles thereof.

18. The method of claim 1, wherein in the exhaust process the textile substrate is treated in a finishing liquor for specific time, temperature and pH which is predetermined, to obtain exhaustion of the at the least one anti-microbial agent onto the textile substrate, wherein the finishing liquor is prepared using the disinfecting treating composition.

19. The method of claim 1, wherein the treated textile substrate is passed through a stenter frame providing heat of between 110° C.-180° C. with a dwell time of between 1-7 minutes.

20. The method of claim 1, wherein the textile substrate passes through a mixture of cross linking agents poured in a finishing bath, followed by passing through a stenter frame which provides heat of between 110° C.-180° C. with a dwell time of between 1-7 minutes.

21. The method of claim 20, wherein the textile substrate is once again passed through the stenter frame for a heat treatment at a temperature of 110° C.-180° C. with a dwell time of 1-7 minutes, in order to penetrate the solution completely in to the textile and complete polymerization.

22. The method of claim 1, wherein the disinfecting treating composition is used in a concentration range of between 0.1 to 4%.

23. The method of claim 1, wherein a quaternary ammonium organosilane compound having the molecular structure, Organosilane quaternary amine
Molecular Structure:

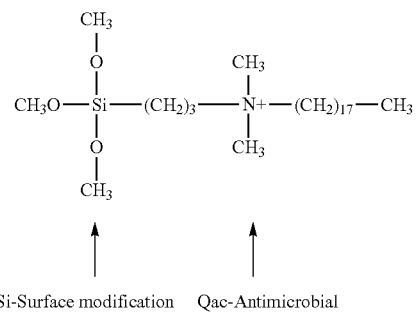

is used in the range between 0.1 to 2%.

24. The method of claim 1, wherein a quaternary ammonium organosilane compound having the molecular structure, Organosilane quaternary amine
Molecular Structure:

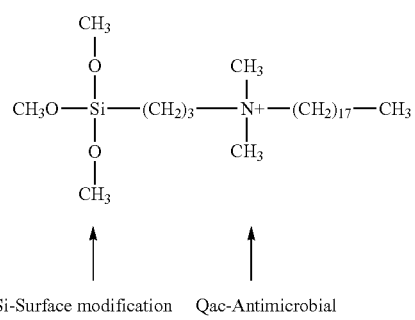

is used in the range of 1 to 2%.

25. The method of claim 1, wherein a silver acrylate salt of the disinfecting treating composition is used in the range of 0.1-2%

Silver acrylate salt

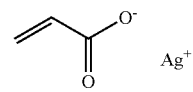

and the polyhexamethylene biguanide (PHMB) used in the range of 1 to 2%, or 2 to 50 grams by weight,
Polyhexamethylene Biguanide (PHMB)

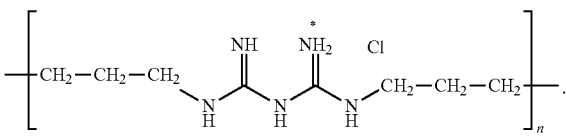

PHMB where n is about 16

26. The method of claim 1, wherein a silver acrylate salt of the disinfecting treating composition is used in the range of 0.5 to 2%

Silver acrylate salt

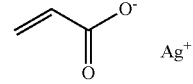

and the polyhexamethylene biguanide (PHMB) used in the range of 1 to 2%, or 2 to 50 grams by weight,
Polyhexamethylene Biguanide (PHMB)

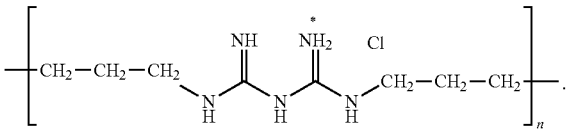

PHMB where n is about 16

* * * * *